E. F. HERRINGTON

Harvester Pitman, Guide and Holder

No. 6,514. Reissued June 29, 1875.

WITNESSES

H. J. Herrington

S. S. Longdon

INVENTOR

E. F. Herrington

THE GRAPHIC CO. PHOTO-LITH. 39 & 41 PARK PLACE, N.Y.

UNITED STATES PATENT OFFICE.

EPHRAIM F. HERRINGTON, OF WEST HOOSICK, NEW YORK.

IMPROVEMENT IN HARVESTER-PITMEN GUIDES AND HOLDERS.

Specification forming part of Letters Patent No. 153,436, dated July 28, 1874; reissue No. 6,514, dated June 29, 1875; application filed February 8, 1875.

*To all whom it may concern:*

Be it known that I, EPHRAIM F. HERRINGTON, of West Hoosick, in the county of Rensselaer and State of New York, have invented certain new and useful Improvements in Harvester-Pitmen Guides and Holders, of which the following is a specification, reference being had to the accompanying drawings, which make part of this specification, and in which—

Figure 1:
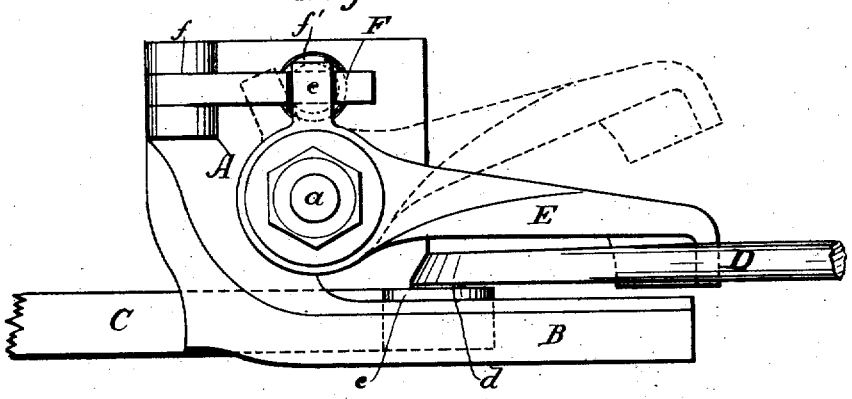
Figure 2:
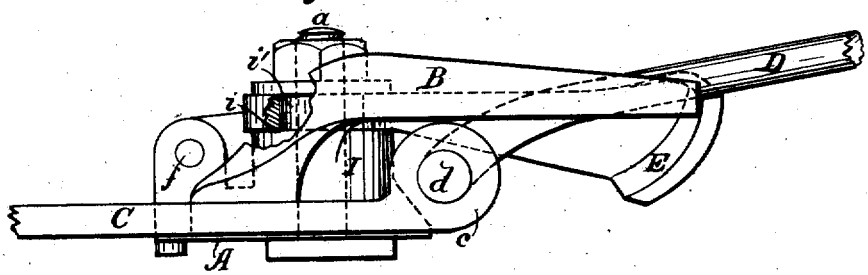
Figure 3:
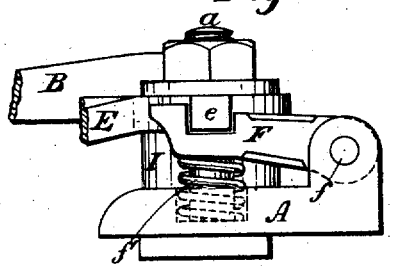

Figure 1 represents a top or plan view of my improved apparatus. Fig. 2 is a front view thereof; and Fig. 3, a rear elevation of a portion of the same.

It is the object of my invention to secure the pitman of a harvester in proper position, while in operation, in such manner as readily to admit of its removal from and adjustment in the eye of the sickle; to which end my invention consists in mounting upon a base or clip, such as that which ordinarily secures the finger-beam and shoe together, a fixed arm or horn, under which the sickle traverses, and a pivoted guide locked in working position by a stop or catch, so that the movement of the pitman is controlled while in operation by the horn and guide, and yet the pitman may be removed from the sickle-eye or inserted therein, when desired, by swinging the guide out of the way.

The base A, upon which the apparatus is mounted, forms the clip which ordinarily secures the finger-beam and shoe together, and also holds the sickle down upon the finger-beam, the bolt *a*, which forms this connection, being in practice made long enough for this purpose. The holding arm or horn B, which projects from the base or clip A, and under which the sickle-eye traverses, is of well-known form. The sickle C is provided with an eye, *c*, in which the hook *d* of the pitman D fits. The pitman is held in place by guide E, between which and the horn B the pitman works.

This guide, as heretofore constructed, has been bolted rigidly to the base, thus necessitating the removal of the guide in order to take out or replace the sickle. In order to obviate this objection, I pivot this guide upon the base so that it shall be capable of swinging horizontally around its fulcrum, which, in this instance, is a post through which the bolt *a* passes, as shown in dotted lines in Fig. 1. When thus swung out of the way the pitman can be readily removed or replaced.

To lock the guide in its working position I form a stud or bolt, *e*, upon the guide E, which stud takes into a spring-catch, F, pivoted at *f* on the base A, so as to play freely up and down, and is held up by a spring, *f'*. This catch can readily be released from the stud by bearing down upon it. The bolt *a* in this instance passes through a short tubular post, I, around which the guide E swings. A shoulder is formed on the post to support the guide, and the post extends through and above said guide far enough to allow it to work freely when the nut attached to the bolt *a* is firmly screwed down upon a washer or collar, resting on top of the post and extending out sufficiently far over the guide to keep it in position. The guide is thus relieved from friction.

A nut and loose thimble may be substituted for the solid base and tubular post above described, if desired; but I prefer the way I have shown.

I claim as of my invention—

1. A pitman-guide mounted upon the clip, substantially as hereinbefore set forth.

2. The combination, substantially as hereinbefore set forth, of the clip or base, the holding arm or horn, and the guide pivoted to the clip.

3. The combination, substantially as hereinbefore set forth, of the clip, post, a holding arm or horn, a pivoted guide, and the spring stop or catch to hold the guide in position.

4. The combination, substantially as hereinbefore set forth, of the clip, the post, the pivoted guide, its arm, and the spring-stop acting on the arm.

E. F. HERRINGTON.

Witnesses:

H. J. HERRINGTON,

S. S. CONGDON.